US011498939B2

(12) United States Patent
Simon et al.

(10) Patent No.: US 11,498,939 B2
(45) Date of Patent: Nov. 15, 2022

(54) GLUCOSE POLYMERS FOR PERITONEAL DIALYSIS (71) Applicant: ROQUETTE FRERES, Lestrem (FR)

(72) Inventors: Denis Simon, Leffrinckoucke (FR); Olaf Haeusler, Fletre (FR); Solène Bock, Lambersart (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 16/332,169

(22) PCT Filed: Sep. 14, 2017

(86) PCT No.: PCT/FR2017/052446
§ 371 (c)(1),
(2) Date: Mar. 11, 2019

(87) PCT Pub. No.: WO2018/051020
PCT Pub. Date: Mar. 22, 2018

(65) Prior Publication Data
US 2019/0300558 A1 Oct. 3, 2019

(30) Foreign Application Priority Data
Sep. 15, 2016 (FR) .................................. 16 58648

(51) Int. Cl.
*A61K 31/718* (2006.01)
*C08B 33/00* (2006.01)
*C07H 3/00* (2006.01)
*A61K 31/70* (2006.01)
*C07H 1/00* (2006.01)
*A23L 29/30* (2016.01)
*A23L 29/20* (2016.01)
*A23L 33/125* (2016.01)
*C08B 31/00* (2006.01)
*A23L 33/10* (2016.01)
*C08L 3/12* (2006.01)
*A23L 13/40* (2016.01)

(52) U.S. Cl.
CPC .............. *C07H 3/00* (2013.01); *A23L 13/426* (2016.08); *A23L 29/20* (2016.08); *A23L 29/35* (2016.08); *A23L 33/10* (2016.08); *A23L 33/125* (2016.08); *A61K 31/70* (2013.01); *A61K 31/718* (2013.01); *C07H 1/00* (2013.01); *C08B 31/00* (2013.01); *C08B 33/00* (2013.01); *C08L 3/12* (2013.01)

(58) Field of Classification Search
CPC ......... C08B 31/00; C08B 33/00; A61K 31/70; A61K 31/718; C07H 1/00; C08L 3/12; C08L 3/02
See application file for complete search history.

(56) References Cited

U.S. PATENT DOCUMENTS

| 3,928,135 | A | 12/1975 | Milner |
| 6,770,148 | B1 * | 8/2004 | Naggi ....................... A61P 7/08 127/71 |
| 6,919,326 | B1 | 7/2005 | Miyata |
| 7,612,198 | B2 * | 11/2009 | Fuertes ................... C08B 35/00 536/102 |
| 8,445,460 | B2 * | 5/2013 | Deremaux ........... A61K 31/718 514/54 |
| 2002/0085410 | A1 | 5/2002 | Antrim |
| 2006/0032400 | A1 | 2/2006 | Henning |
| 2008/0241904 | A1 | 10/2008 | Kubota et al. |
| 2012/0295873 | A1 * | 11/2012 | Guerin-Deremaux ..................... C08B 30/20 514/60 |

FOREIGN PATENT DOCUMENTS

| EP | 1 369 432 A2 | 12/2003 |
| EP | 1 548 033 A2 | 6/2005 |
| JP | 2008095117 A | 4/2008 |
| WO | 2010032510 A1 | 3/2010 |
| WO | 2011095736 A1 | 8/2011 |

OTHER PUBLICATIONS

Fuertes, P. et al., machine English translation of EP1548033A2, 16 pages; original document published 2005 (Year: 2005).*
Van Den Einde, R.M. et al., Journal of Food Science, "Understanding Molecular Weight Reduction of Starch During Heating-shearing Processes", 2003, vol. 68, No. 8, pp. 2396-2404 (Year: 2003).*
The English translation of the International Search Report, dated Nov. 9, 2017, in the corresponding PCT Appl. No. PCT/FR2017/052446.

* cited by examiner

*Primary Examiner* — Bahar Craigo (57) ABSTRACT

The invention relates to a novel glucose polymer which is particularly useful for administration by the parenteral route, and to the method for the production thereof. The invention also relates to compositions comprising such a glucose polymer, and to the methods for the production thereof. The invention further relates to the use thereof as a medicament, for example as an osmotic agent for peritoneal dialysis.

15 Claims, 2 Drawing Sheets

Figure 1

* Coloring of the solution observed upon sterilization

Figure 2

* Coloring of the solution observed upon sterilization

Figure 3

GLUCOSE POLYMERS FOR PERITONEAL DIALYSIS

CROSS-REFERENCE TO RELATED APPLICATIONS

This application is a National Stage Application of PCT/FR2017/052446 filed Sep. 14, 2017, which claims priority from French Patent Application No. 16 58648, filed on Sep. 15, 2016. The priority of said PCT and French Patent Application are claimed. Each of the prior mentioned applications is hereby incorporated by reference herein in its entirety.

The present invention relates to a novel glucose polymer which is particularly useful for parenteral administration, and also to a method for producing same. The invention also relates to compositions comprising such a glucose polymer, and also to the methods for producing said compositions. Finally, the invention relates to the use thereof as a medicament, for example an osmotic agent for peritoneal dialysis.

CONTEXT OF THE INVENTION

Dialysis is a process aimed at supplementing or replacing kidney function in certain patients. To do this, the methods principally used at the current time are hemodialysis and peritoneal dialysis.

In hemodialysis, the patient's blood passes through a kidney dialysis machine comprising a membrane which acts as an artificial kidney, in order to filter and purify the blood. Because this is an extracorporeal treatment which requires special equipment, hemodialysis inevitably comes up against certain drawbacks such as the availability of dialysis machines and the possibility of infections and contaminations.

Peritoneal dialysis does not require such equipment, since it advantageously uses the patient's peritoneum as a filtering membrane. The peritoneum is an abdominopelvic membranous coating of the body walls which is capable of acting as a natural semi-permeable membrane, owing to its large number of blood vessels and capillaries. The treatment consists in introducing a peritoneal dialysis solution into the peritoneal cavity via a catheter. During a predetermined exposure time, an exchange of fluids and solids occurs between the solution and the blood, until equilibrium is reached. The dialysis solution or dialysate is then discharged from the body by a catheter.

Peritoneal dialysis solutions are sterile and conventionally comprise water, electrolytes ($Na^+$, $Cl^-$, $Ca^{2+}$, $Mg^{2+}$), a buffer (lactate and/or carbonate) and an osmotic agent.

The role of the osmotic agent is to make the dialysis solution slightly hypertonic. Fluid and solute movements thus occur, from the blood to the dialysate, by a gradient effect.

Conventional solutions use glucose as osmotic agent, glucose being an inexpensive compound which has the advantage of producing high degrees of ultrafiltration.

However, a major drawback is that these solutions are not biocompatible. The principal factor responsible for these bioincompatibility problems lies in the presence of high glucose contents and of glucose degradation products (GDPs), and also in the low pH of these solutions.

GDPs are low-molecular-weight molecules, among which are principally 5-hydroxymethylfuraldehyde (5-HMF), and also for example furaldehyde and 3,4-dideoxyglucosone-3-ene (3,4-DGE). GDPs cause abdominal pain, feelings of discomfort during the perfusion, and are cytotoxic. They inhibit cell proliferation and are detrimental to the functions of inflammatory cells. 3,4-DGE, for example, is lethal for leukocytes and mesothelial cells at the concentrations usually found in peritoneal dialysis solutions. GDPs also promote the production of advanced glycation end products (AGEs), which cause protein and cell-function dysfunctions.

Furthermore, the acidity of dialysis solutions causes irritations of the peritoneal wall, which causes many patients to reject peritoneal dialysis after a few years.

The presence of GDPs and the low pH of these solutions are closely linked problems, and this link explains why it is difficult to reconcile a low GDP content and physiological pH (from 7.35 to 7.45). It is now well established that GDPs are generated during an essential step of heat sterilization of the glucose solution. In point of fact, the amount produced depends mainly on the pH of the solution subjected to sterilization. The lower the sterilization pH, the less GDPs will be generated. It has thus been determined that the optimum sterilizing pH for minimizing GDP production is from 2.0 to 3.1. It is, however, clear that solutions as acidic as this could not be administered to patients. Conversely, the higher the sterilization pH, the more GDPs will be generated. Added to these phenomena is the fact that the GDPs produced lower the pH of the solution.

As a result of all this, the current solutions are the least poor of the compromises between pH and GDP content. The conventional solutions thus conventionally have a pH of approximately 5.5 and a relatively high GDP concentration.

In order to minimize these defects, two approaches have been developed.

The first approach is based on a method using two separate solutions, conventionally contained in two-compartment or three-compartment bags. A first solution comprises the glucose, which is sterilized apart under very acidic conditions, in order to minimize GDP formation. A second solution comprises the buffer at a high pH. These two solutions are then mixed in order to obtain a solution having reduced amounts of GDPs and a pH approaching physiological pH. A major drawback of this approach is that this mixing step, in addition to making the method complex, increases the risks of contamination.

The second approach is based on the development of new osmotic agents which can to a greater extent be considered to be biocompatible. In this regard, mention may be made of the only two alternatives to glucose at the current time available on the market: amino acids and icodextrin, a glucose polymer belonging to the maltodextrin family, obtained by starch hydrolysis.

The use of glucose polymers such as icodextrin is an attractive alternative to glucose. In addition to limiting the exposure to glucose and to GDPs, these compounds allow a longer-lasting and linear ultrafiltration. Furthermore, their effectiveness is independent of the peritoneal permeability to small solutes, which means that it is possible to maintain the ultrafiltration during periods of peritonitis.

However, icodextrin cannot strictly be considered to be biocompatible, because of its glucosidic nature. Even if it is to a lesser extent, the heat-sterilization of icodextrin also results in the production of toxic GDPs, and the pH of the dialysis solutions containing it remains low (5-6).

In order to decrease this amount of GDPs in icodextrin, it has recently been proposed, in U.S. Pat. No. 6,770,148 B1 (BAXTER) to use icodextrins that have been modified by reduction, oxidation and glycosylation reaction.

This technology has made it possible to reduce the amounts of GDPs produced, but without however eliminating them. Moreover, the problem of the low pH of the dialysis solutions is not solved by this technology.

The objective of the present invention is to provide osmotic agents which make it possible to overcome the abovementioned drawbacks, linked to the use of glucose or of glucose polymers of the prior art. The intention of the present invention is in particular to provide glucose polymers allowing the preparation of solutions for parenteral administration which have extremely low GDP contents. The objective of the present invention is also to provide glucose polymers which allow the preparation of solutions at a pH close to physiological pH, this being without recourse to the use of two-compartment or three-compartment bags. The objective of the present invention is to solve these problems by providing osmotic agents which also have good pharmacokinetic properties.

Presentation of the Invention

It is to the credit of the applicant to have succeeded in solving the abovementioned problems, by virtue of the development of a novel glucose polymer.

The novel glucose polymer proposed by the applicant is a modified glucose polymer, in particular obtained from starch, characterized in that it is obtained by branching and reduction of a starch having an amylose content of at least 10%, said polymer having an α-1,6-bond content of less than 20%.

Without wanting to be bound by any theory, the applicant is of the opinion that this results in products which have a particular three-dimensional structure, very suitable for the applications targeted by the present invention.

The best results have in particular been obtained with a starch having an α-1,6-bond content (or "branching content") of at least 10%, in particular of at least 12%, but absolutely less than 20%.

The best results have also been obtained with a starch having an amylose content of greater than 25%, in particular of at least 30%. The results are even better with a starch having an amylose content of greater than 40%, or even greater than 50%.

U.S. Pat. No. 6,770,148 B1 mentioned above does not describe branched starches, and consequently does not make it possible to solve the problem of the invention, as is apparent on reading the examples below.

The novel glucose polymers of the invention allow the production of solutions in which, after sterilization, the GDPs are not detectable, this being despite the high pH of the solution, which makes it possible to envision the production of solutions having a pH close to physiological pH, without having recourse to methods using two-compartment or three-compartment bags.

Furthermore, the glucose polymers of the invention have good pharmacokinetic properties, in particular better than that obtained with low-amylose starches and/or with starches having branching contents that are too high.

SUMMARY OF THE INVENTION

The first subject of the invention is thus a glucose polymer characterized in that it is obtained by branching and reduction of a starch having an amylose content of at least 10%, and in that said glucose polymer has an α-1,6-bond content of less than 20%.

A subject of the invention is also a method for producing such a glucose polymer.

A subject of the invention is also a composition comprising such a glucose polymer, in particular a pharmaceutical composition such as, for example, a peritoneal dialysis solution.

A subject of the invention is also a method for producing such a composition.

A subject of the invention is also the use of such a glucose polymer or of such a composition as a medicament and/or in peritoneal dialysis, and/or in peritoneal nutrition, and/or in plasma filling, and/or as an osmotic agent, and/or as a plasma expander, and/or in vaccinology, and/or as an adjuvant, and/or as a protein stabilizer, and/or as a protein carrier.

DETAILED DESCRIPTION OF THE INVENTION

The first subject of the invention is a glucose polymer characterized in that it is obtained by branching and reduction of a starch having an amylose content of at least 10%, and in that it has an α-1,6-bond content of less than 20%.

The glucose polymer of the invention is thus characterized firstly in that it is derived from a starch having an amylose content of at least 10%, this percentage being expressed by dry weight of amylose related to the total dry weight of the starch.

The term "starch" is conventionally intended to mean a starch isolated from any suitable source, for example from plants chosen from cereals, tuberous plants and leguminous plants. This starch is preferably a pea starch or a corn starch.

The amylose content of a starch can conventionally be determined by those skilled in the art by potentiometric determination of the iodine absorbed by the amylose in order to form a complex.

Preferably, this amylose content is at least 20%, preferably at least 30%, preferably at least 35%, preferably at least 40%, preferably at least 45%, preferably at least 50%, preferably at least 55%, preferably at least 60%. It is generally at most equal to 85% or to 80%. This amylose content is for example chosen in a range of from 20% to 85%, preferably from 30% to 80%, preferably from 50% to 75%.

The glucose polymer of the invention is also characterized in that it is obtained by reduction of a starch. This reduction typically results in the conversion of carbonyl groups to hydroxyl groups.

Thus, alternatively or in addition, the glucose polymer of the invention may be defined by the fact that it comprises carbonyl groups converted into hydroxyls.

The glucose polymer of the invention is also characterized in that it is obtained by branching of starch, and in that it has an α-1,6-bond content of less than 20%.

The term "branching" is conventionally intended to mean the fact that the starch is subjected to branching enzymes which form α-1,6-bonds, for example chosen from glycogen-branching enzymes, starch-branching enzymes, or a mixture thereof.

These branches make it possible to achieve α-1,6-bond contents that it is not possible to obtain on a native starch. In particular, this content is conventionally greater than 7%.

On the other hand, this branching content does not exceed 20% in the context of the present invention.

This α-1,6-glucosidic bond content can conventionally be determined by those skilled in the art by proton NMR. Reference may for example be made to the method described in the example in point B. below.

Preferably, this α-1,6-glucosidic bond content is at least 8%, preferably at least 9%, preferably at least 10%, preferably at least 11%, preferably at least 12%. This α-1,6-glucosidic bond content is for example chosen in a range of from 8% to 19%, from 9% to 19%, from 10% to 19%, from 10% to 18%, from 10% to 17%, from 10% to 16% or from 11% to 16%, preferably from 12% to 16%, preferably from 13% to 15%.

Preferably, the glucose polymer according to the invention has a weight-average molecular weight ($M_W$) chosen in a range of from 20 000 to 200 000 daltons (Da), in particular for use in peritoneal dialysis; this $M_W$ being determined by liquid chromatography and detection by differential refractometry, preferably using pullulans for the calibration.

Preferably, this $M_W$ is less than 100 000 Da, in particular for use in peritoneal dialysis, more preferably less than 50 000 Da. It is preferably greater than 25 000 Da. It is for example chosen in the range of from 25 000 to 50 000 Da, preferably from 30 000 to 40 000 Da.

Alternatively or in addition, the glucose polymer of the invention may be defined by its $M_W$ as determined by liquid chromatography with light-scattering detection.

According to this method, the glucose polymer according to the invention preferentially has an $M_W$ of at least 30 000 Da, in particular for use in peritoneal dialysis. This $M_W$ is preferably at least 40 000 Da, preferably at least 50 000 Da, preferably at least 60 000 Da, preferably at least 70 000 Da, preferably at least 80 000 Da, preferably at least 90 000 Da, preferably at least 100 000 Da. It does not generally exceed 1 500 000 Da, or even 1 000 000 Da, or even 800 000 Da, or even 700 000 Da, or even 600 000 Da, or even 500 000 Da, or even 400 000 Da, or even 300 000 Da. Preferably, this $M_W$, in particular for use in peritoneal dialysis, is chosen in a range of from 30 000 to 600 000 Da, preferably from 40 000 to 500 000 Da, preferably from 50 000 to 400 000 Da, preferably from 60 000 to 300 000 Da, for example from 100 000 to 200 000 Da.

Preferably, the polydispersity index (polyD) of the glucose polymer according to the invention is less than 3.0, preferably less than 2.5, more preferably less than 2.0. It is generally greater than 0.5, for example between 1.0 and 3.0, preferably between 1.5 and 2.5.

This polyD corresponds to the ratio between the weight-average molecular weight $M_W$ and the number-average molecular weight $M_N$ of the glucose polymer.

These $M_W$ and $M_N$ can in the present invention be determined by two methods as defined above. Reference may for example be made to methods 1 and 2 described in the example in point B. below.

In one embodiment, the polymer is a maltodextrin, in particular an icodextrin.

Additionally, the glucose polymer according to the invention may also be defined by its pH after sterilization at 121° C. for 45 minutes, which is in a range of from 6 to 8, preferentially from 7 to 8; said pH being measured on the basis of an aqueous 5% solution of said glucose polymer.

Preferentially, the glucose polymer of the invention has, in particular after heat sterilization, in particular at 121° C. for 15 minutes:
  a 5-hydroxymethylfuraldehyde (5-HMF) content of less than 135 ppb, preferably less than 100 ppb, preferably less than 50 ppb, preferably less than 30 ppb, preferably less than 20 ppb, preferably less than 10 ppb, preferably less than 8 ppb, preferably less than 6 ppb, preferably less than 4 ppb, preferably less than 2 ppb; and/or
  a furfuraldehyde content of less than 65 ppb, preferably less than 8 ppb, preferably less than 6 ppb, preferably less than 4 ppb, preferably less than 2 ppb; and/or
  a 3,4-dideoxyglucosone-3-ene (3,4-DGE) content of less than 20 ppm, preferably less than 10 ppm, preferably less than 5 ppm, preferably less than 2 ppm, preferably less than 1 ppm, preferably equal to 0 ppm,
these contents being expressed by weight relative to the weight of a 4% solution of said glucose polymer of the invention prepared in deionized water.

The 5-HMF and furaldehyde contents can be determined by those skilled in the art by liquid chromatography and detection by UV spectrophotometry at 280 nm. The 3,4-DGE content can be determined by those skilled in the art by liquid chromatography, preferably using pyrazine carboxamide for the calibration, and detection by UV spectrophotometry at 230 nm. Reference may for example be made to the methods described in the example in point C.2. below.

Generally, the glucose polymer according to the invention has an osmolality of between 200 and 300 mOsm/kg; said osmolality being determined on the basis of a 0.4% solution of said glucose polymer. This osmolality is for example between 230 and 280 mOsm/kg, or even between 230 and 250 mOsm/kg.

This osmolality may conventionally be determined by those skilled in the art by means of an osmometer. Reference may for example be made to the method described in the example in point B. below.

Preferably, the glucose polymer according to the invention has a reducing sugar content of less than 3.5%, this percentage being expressed by dry weight of reducing sugars relative to the total dry weight of the glucose polymer. This content is preferably less than 2.5%, preferably less than 1.0%, preferably less than 0.5%, preferably less than 0.1%, more preferably less than 0.05%. It is generally greater than 0.001%, or even greater than 0.005%.

This reducing sugar content can conventionally be determined by those skilled in the art by means of the Bertrand method. Reference may for example be made to the method described in the example in point B. below.

Generally and advantageously, the glucose polymer according to the invention is soluble to very soluble in water at ambient temperature (25° C.). The term "soluble to very soluble in water" is conventionally intended to mean that a maximum volume of water of 30 ml is required to dissolve one dry gram of said compound (see for example the reference European Pharmacopeia "1.4. Monographs, July 2014: 10000").

The glucose polymer of the invention may comprise other modifications, as long as that does not contravene the properties sought in the present invention, in particular in terms of efficacy and innocuousness. These modifications may be of physical and/or chemical type. The glucose polymer may for example be substituted. However, generally and advantageously, the glucose polymer of the invention is not substituted, that is to say in particular that it is not esterified and/or etherified.

A subject of the present invention is also a method, which is particularly useful for producing a glucose polymer in accordance with the invention, which comprises subjecting a starch having an amylose content of at least 10% to:
  (a) a branching step; and
  (b) a reduction step.

The branching step can be carried out by means of a branching enzyme, for example glycogen-branching enzymes, starch-branching enzymes, or a mixture thereof.

Such enzymes are commercially available. Mention may for example be made of the BRANCHZYME® product (Novozyme).

The reduction can be carried out by any technique known to those skilled in the art, for example by means of the use of sodium tetrahydroborate or of dihydrogen, optionally in the presence of a catalyst such as Raney nickel.

Preferably, the branching step is carried out before the reduction step. Thus, the operating conditions for the reduction are such that they allow the conversion of the reducing functions into hydroxyls without impairing the hyperbranched structure of the glucose polymer. In particular, the pH is adjusted during the reduction step in order to be sure not to damage the hyperbranched structure of the product, that is to say so as not to oxidize or hydrolyze the product.

For example, for a reduction with sodium tetrahydroborate, the reaction can be carried out at a temperature of approximately 40° C. for a reaction time which makes it possible to obtain the lowest possible reducing sugar content while at the same time maintaining the hyperbranched structure of the starch, for example approximately 20 h.

With hydrogenation/Raney Ni, the reaction can for example be carried out at approximately 120° C. for approximately 2-4 h.

Preferably, the method also comprises a hydrolysis step, preferably by means of an enzymatic treatment, preferably by means of a β-amylase and/or of an amyloglucosidase.

Preferably, this hydrolysis step is subsequent to the branching step. It is preferably prior to the reduction step.

Preferably, the method of the invention comprises a prior step of dissolving the starch, preferably by heating (also commonly known as "cooking the starch").

The method may moreover comprise an additional step of chromatography, in particular so as to reduce the polyD of the glucose polymer to be obtained.

The starch can then be purified and/or dried by any technique known to those skilled in the art.

Treatment examples useful for (total or partial) purification of the glucose polymer of the invention are filtration, ultrafiltration, treatment with active carbon, these treatments possibly being combined together.

For the drying, use may for example be made of spray-drying.

A subject of the present invention is also a composition comprising the glucose polymer of the invention, in particular a pharmaceutical composition. Thus, the composition may comprise a pharmaceutically acceptable carrier or excipient.

It may be a solution that is ready to be administered, in particular parenterally, for example a preferentially aqueous and sterile solution. It may also be a composition which is useful for producing a solution intended to be administered. In the latter case for example, it may be a ready-to-use pulverulent composition, which can be reconstituted by simply adding water, before being sterilized and/or administered.

Preferably, the solution to be administered is chosen from a peritoneal dialysis solution, a parenteral nutritional solution and a plasma filling solution. It is most preferentially a peritoneal dialysis solution.

Generally, in the solution to be administered of the invention, the concentration of glucose polymer of the invention is chosen in a range of from 1% to 20%, preferably from 1% to 15%, preferably from 1% to 10%. This concentration is preferably at least 2%, preferably at least 3%, preferably at least 4%. It is for example chosen in the range of from 4% to 10%, preferably from 5% to 9%, preferably from 6% to 9%, for example from 7% to 8%.

Preferably, when this composition is a peritoneal dialysis solution, it is hypertonic. It thus preferably has an osmolality of greater than 280 mOsm/kg, preferably greater than 320 mOsm/kg.

Preferably, when this composition is a solution for parenteral nutrition, or for plasma filling, it is isotonic. It thus preferably has an osmolality chosen in a range of from 260 to 340 mOsm/kg, ideally in a range of from 280 mOsm/kg to 320 mOsm/kg.

Preferably, the composition according to the invention has a pH chosen in a range of from 6.00 to 9.00, preferably from 7.00 to 8.00, in particular from 7.30 to 7.50, for example from 7.35 to 7.45.

Preferentially, the composition of the invention, in particular the solution intended to be administered, in particular after heat sterilization, has:
  a 5-hydroxymethylfuraldehyde (5-HMF) content of less than 135 ppb, preferably less than 100 ppb, preferably less than 50 ppb, preferably less than ppb, preferably less than 20 ppb, preferably less than 10 ppb, preferably less than 8 ppb, preferably less than 6 ppb, preferably less than 4 ppb, preferably less than 2 ppb; and/or
  a furfuraldehyde content of less than 65 ppb, preferably less than 8 ppb, preferably less than 6 ppb, preferably less than 4 ppb, preferably less than 2 ppb; and/or
  a 3,4-dideoxyglucosone-3-ene (3,4-DGE) content of less than 20 ppm, preferably less than 10 ppm, preferably less than 5 ppm, preferably less than 2 ppm, preferably less than 1 ppm, preferably equal to 0 ppm;
these contents being expressed by weight relative to the weight of said composition when it is in the form of a 4% solution of said glucose polymer of the invention.

Generally, the composition of the invention comprises other substances, provided that this does not contravene the properties sought in the present invention, in particular in terms of innocuousness and efficacy. These other substances are typically chosen from:
  active agents, for example (i) osmotic agents, and/or plasma expanders and/or parenteral nutrition agents other than the glucose polymer of the invention, for example icodextrin, glucose, dextrans, hydroxyethyl starch, (ii) therapeutic proteins, for example vaccines, antibodies;
  buffers, for example lactate or citrate buffers;
  electrolytes.

However, preferably, the substance of the invention represents at least 50% by dry weight of the osmotic agents, and/or of the plasma expanders and/or of the parenteral nutrition agents of the composition, preferably at least 60%, preferably at least 70%, preferably at least 80%, preferably at least 90%. Very preferentially, the substance of the invention is the only osmotic agent and/or plasma expander and/or parenteral nutrition agent of the composition of the invention.

The invention also relates to the use of a glucose polymer according to the present invention for producing a peritoneal dialysis composition, and/or a parenteral nutrition composition, and/or a plasma filling composition, and/or as an osmotic agent, and/or as a plasma expander, and/or for producing a vaccine, in particular as an adjuvant, and/or for stabilizing proteins, and/or as a protein carrier.

A subject of the invention is also a method for producing a composition according to the invention, in particular a peritoneal dialysis solution, which comprises mixing the polymer of the invention with at least one other substance, in particular as defined above for the composition of the invention, and/or with a solvent, preferentially water.

Preferably, this method comprises a step of sterilizing said composition, preferably heat-sterilizing.

The invention also relates to the use of a glucose polymer or of a composition according to the invention, as a medicament. The present invention also relates to a treatment method, comprising the administration of a glucose polymer or of a composition according to the invention, to a patient who is in need thereof.

Preferably, the glucose polymer or the composition of the invention is for parenteral use.

The glucose polymer is particularly suitable for use in peritoneal dialysis, in particular as an osmotic agent. Thus, the present invention relates to a glucose polymer according to the present invention, for use thereof in peritoneal dialysis, in particular in a peritoneal dialysis solution, in particular as an osmotic agent. It also relates to the use of a glucose polymer according to the present invention for producing a peritoneal dialysis solution, in particular intended for the treatment of chronic renal failure. The present invention also relates to a method for treating chronic renal failure by peritoneal dialysis in a subject, comprising the administration of a dialysis solution comprising the glucose polymer according to the present invention to said subject, in particular by injection into the peritoneal cavity.

It can be used as a supplement or in the place of glucose solutions, typically in the context of continuous ambulatory peritoneal dialysis (CAPD) or of automated peritoneal dialysis (APD).

The glucose polymer of the invention can also be used in other applications wherein a parenteral administration is desired, for example for use in parenteral nutrition, in plasma filling, in particular as a plasma expander or in vaccinology, in particular as an adjuvant, or as a protein stabilizer, or as a protein carrier.

For an application in peritoneal dialysis, the medicament of the invention is typically intended for a patient suffering from renal failure. That is to say having a total or partial loss of renal function, subsequent for example to diabetes or to an infection. Thus, the present invention relates to a glucose polymer according to the invention for use thereof in a peritoneal dialysis solution. It also relates to the use of a glucose polymer according to the present invention for producing a peritoneal dialysis solution, in particular intended for the treatment of renal failure. The present invention also relates to a method for treating renal failure, comprising the administration of a peritoneal dialysis solution comprising the glucose polymer according to the present invention to said subject.

For an application in plasma filling, the medicament of the invention is typically intended for a patient suffering from hypovolemia, typically caused by a rupture of the continuity of the vascular compartment, for example subsequent to a trauma, a surgical procedure, or a burn. Thus, the present invention relates to a glucose polymer according to the present invention, for use thereof in a plasma filling solution. It also relates to the use of a glucose polymer according to the present invention for producing a plasma filling solution, in particular intended for the treatment of hypovolemia. The present invention also relates to a method for treating hypovolemia in a subject, comprising the administration of a plasma filling solution comprising the glucose polymer according to the present invention to said subject.

For an application in parenteral nutrition, the medicament of the invention is typically intended for a patient in whom enteral or oral nutrition is not possible, for example a patient suffering from intestinal failure or from food intolerance with vomiting. Thus, the present invention relates to a glucose polymer according to the present invention for use thereof in a parenteral nutrition solution. It also relates to the use of a glucose polymer according to the present invention for producing a parenteral nutrition solution, in particular intended for the treatment of intestinal failure or of food intolerance with vomiting. The present invention also relates to a method of parenteral nutrition in a subject, comprising the administration of a parenteral nutrition solution comprising the glucose polymer according to the present invention to said subject, said subject possibly suffering from intestinal failure or from food intolerance with vomiting.

It should be noted that, in the present invention, it is understood that the expression between X and Y covers a range of values excluding the limits cited, whereas the expression "chosen in the range of from X to Y" covers a range of values including the limits cited.

In the present invention, it is moreover understood that, when reference is made to a concentration expressed as percentage of a substance in solution, this concentration indeed expresses the number of grams of said substance per 100 ml of said solution. This weight in grams is indeed a dry weight, that is to say that it excludes in particular the weight of water possibly present in the substance in its pulverulent form, before dissolution.

The invention will be understood more clearly by means of the examples which follow, which are intended to be illustrative and nonlimiting.

EXAMPLES

A. Substances Tested

1. Glucose Polymer According to the Invention [HSB-red])

The starch used had an amylose content of 65% (EURYLON® 7, Roquette). A starch starch milk (suspension) containing 10% solids and at a pH of 7.5 was cooked at 160° C. The paste obtained was cooled to 75° C., and the pH was adjusted to 7.0.

The starch was then subjected to a branching step by means of a branching enzyme (BRANCHZYME®, Novozymes), used in a proportion of from 625 to 1000 U/g dry of starchy matter, for 22 hours at 65° C. and at pH 7.0. The reaction medium was then cooled to 48° C., and the pH was adjusted to 5.5.

The branched starch thus obtained was subjected to a hydrolysis step by means of a β-amylase (OPTIMALT® BBA, Genencor International), used in a proportion of from 1 to 4 U/g dry of starchy matter, for 2 hours at 48° C. and at a pH of 5.5. The enzyme was then deactivated by heating for 1 hour at 85° C. The reaction mixture was cooled to 50° C. and the pH was adjusted to 3.5.

The reaction product was centrifuged at 5000 rpm, and the supernatent was collected.

A solution containing 30% of branched starch thus obtained was prepared. Dissolution was promoted by heating at 90° C., then the temperature was lowered to 40° C. The pH was adjusted to 10.5 with sodium hydroxide (3% NaOH).

The starch in solution was subjected to a reduction step by means of 200 mol % of $NaBH_4$ relative to the reducing functions. At the end of the reaction, the pH was adjusted to 6.5. 18% $H_2SO_4$ was added to the reaction product.

The solution was dialyzed on a 1000 Da membrane overnight. The product thus obtained was dried in a rotary evaporator and milled with a knife mill.

2. Comparative Glucose Polymers ([ICO-Red], [ICO], [HBS])

The [ICO] product corresponds to an unmodified icodextrin, that is to say a non-reduced icodextrin.

In order to produce the [ICO-red] product, a reduced icodextrin of the prior art in accordance with U.S. Pat. No. 6,770,148 was prepared by reduction of an icodextrin. For the reduction, the process was carried out as described in point 1. above.

The [HBS] product corresponds to a product obtained by branching of starch, but which has not undergone reduction. For the branching, and as described in point 1. above, the glucose polymer was branched by means of a branching enzyme and subjected to a hydrolysis step by means of a β-amylase.

3. Glucose (Reference)

The glucose used was anhydrous dextrose (ROQUETTE).

B. Characterization of the Glucose Polymers Used

The characterization of the [HBS-red] glucose polymers according to the invention, and of the comparative [ICO-red], [ICO], [HBS] glucose polymers were determined according to the following methods.

1. Determination of the α-1,6-bond content. The α-1,6-bond content was determined by proton NMR. The α-1,6-glucosidic bond content, expressed as percentages, corresponds to the amount of signal of the proton carried by the C1 of an anhydroglucose unit which bonds another anhydroglucose unit via an α-1,6-bond, when a value of 100 has been given to all of the signals of the glucosidic protons carried by all the C1 of the residues of said glucose polymers.

2. Determination of the osmolality. The osmolality was determined on the basis of an aqueous solution prepared in deionized water comprising 0.4% of glucose polymer. The measurement of the osmolality of this solution was carried out using an osmometer (FISKE® ASSOCIATES MARK 3), according to the constructor's indications.

3. Determination of the weight-average ($M_W$) and number-average ($M_N$) molecular weights, and calculation of the polydispersity index (polyD). The average molecular weights $M_W$ and $M_N$ were determined according to two methods.

Method 1: liquid chromatography (using pullulans of various $M_W$ for the calibration) and detection by differential refractometry.

A set of columns (Shodex OH pak SB—800 QH) composed of the following columns was used:

a column with a particle size of 8 μm, a pore size of 100 Å, an internal diameter of 8.0 mm and a length of 300 mm (OH pak SB—802 HQ—Waters ref. JWE 034256)

a column with a particle size of 6 μm, a pore size of 800 Å, an internal diameter of 8.0 mm and a length of 300 mm (OH pak SB—803 HQ—Waters ref. JWE 034257)

a column with a particle size of 13 μm, a pore size of 7000 Å, an internal diameter of 8.0 mm and a length of 300 mm (OH pak SB—805 HQ—Waters ref. JWE 034259).

The pullulan standards used (Waters kit—Ref. JWE034207) had the following $M_W$ (Da): 78 000, 40 400; 211 000; 112 000; 47 300; 22 800; 11 800; 5900.

The elution solvent was an aqueous 0.2 M sodium nitrate solution containing 0.02% of sodium azide, filtered on a 0.02 μm filter. The flow rate of the mobile phase for the chromatography was 0.5 ml/min.

Method 2: liquid chromatography with detection by light scattering (RI detector and light scattering detector, DAWN-HELEOS II).

A set of columns composed of the following columns was used:

a column with a particle size of 10 μm, a pore size of 100 Å, an internal diameter of 8.0 mm and a length of 300 mm (PSS SUPREMA 100—Ref. SUA0830101E2);

a column with a particle size of 10 μm, a pore size of 1000 Å, an internal diameter of 8.0 mm and a length of 300 mm (PSS SUPREMA 1000—Ref. SUA0830101E3).

The elution solvent was an aqueous 0.1 M sodium nitrate solution containing 0.02% of sodium azide filtered on a 0.02 μm filter, and the dilution solvent was dimethyl sulfoxide (DMSO) containing 0.1 M of sodium nitrate. The flow rate of the mobile phase for the chromatography was 0.5 ml/min. The calibration was carried out with a pullulan (Pullulan P50, Shodex).

4. Determination of the reducing sugar content. The reducing sugar content was determined by the Bertrand method. More specifically, the following were introduced into a 250 ml conical flask: 20 ml of solution to be titrated containing the equivalent of 0.5 to 5.0 mg of glucose per ml; 20 ml of cupric solution (4% of copper sulfate pentahydrate); 20 ml of sodium tartrate solution (20% of sodium potassium double tartrate and 15% of sodium hydroxide); some glass beads. The whole mixture was heated to moderate boiling for 3 minutes and then left to separate out for 2 minutes. The supernatant was removed, and the $Cu_2O$ precipitate was dissolved in 20 ml of ferric liquor (5% of ferric sulfate and 20% of sulfuric acid). The solution obtained was titrated with a solution of potassium permanganate at 0.1 N, and using the Bertrand table.

The results are presented in Table 1.

TABLE 1

| | [HBS-red] | [ICO-red] | [ICO] | [HBS] |
|---|---|---|---|---|
| Reducing sugars (% dry) | <0.05 | 0.299 | 1.9 | 1.93 |
| α-1,6-bond content (%) | 14 | 7 | 7 | 14 |
| $M_W$ (Da, method 1) | 34 920 | 13 830 | 13 550 | 34 930 |
| $M_N$ (Da, method 1) | 19 850 | 7670 | 7280 | 18 690 |
| polyD | 1.8 | 1.8 | 1.9 | 1.9 |
| $M_w$ (Da, method 2) | 125 000 | 22 000 | 21 000 | 130 000 |
| Osmolality (mOsm/kg) | 240 | 241 | 240 | 240 |

C. Glucose Polymer Tests

1. Effects of the Sterilization on pH

In this example, the inventors studied the influence of sterilization on the pH of solutions using various glucose polymers or glucose (positive control).

20 ml solutions containing 5% by dry weight of each of the substances to be tested were prepared in deionized water. The pH was measured after sterilization at 121° C. for 15 or 45 minutes, on the stirred solutions.

Figure 1:
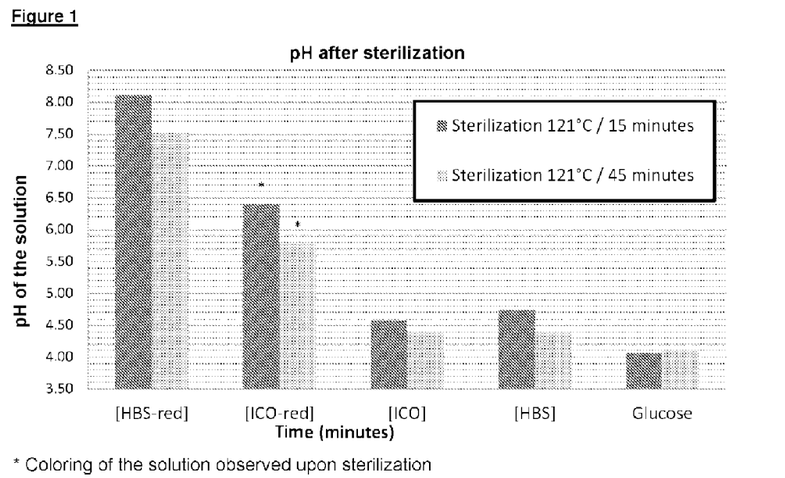
FIG. 1: Influence of sterilization on the pH of solutions using various glucose polymers or glucose (positive control), the pH being measured after sterilization at 121° C. for 15 or 45 minutes.

The results are presented in FIG. 1.

The glucose polymer in accordance with the invention [HBS-red] is that which presents the pH closest to that of physiological pH after sterilization. This is not the case with the comparative polymers [ICO-red], [ICO] and [HBS], which present acidic pHs after sterilization, below 6.5, or even 6.0; that is to say differences of more than 1 pH unit compared to physiological pH.

Furthermore, the inventors noted that an unwanted brown coloring appeared when the [ICO-red] glucose polymer was sterilized.

2. Effects of the Sterilization on GDP Production

In this example, the inventors studied the influence of sterilization on the production of GDPs, namely 5-hydroxymethyl furaldehyde (5-HMF), furaldehyde and 3,4-dideoxyglucosone-3-ene (3,4-DGE), of solutions using various glucose polymers or glucose.

20 ml solutions containing 4% of each of the substances to be tested were prepared in deionized water. The GDP content was measured after sterilization at 121° C. for 15 minutes.

The 5-HMF and furaldehyde content was determined by liquid chromatography using 5-HMF standards (Merck—Ref. 8.206.78.001) or furaldehyde standards for the calibration respectively), and detection by UV spectrophotometry at 280 nm. For the chromatography, a column with a particle size of 9 μm, 8% crosslinking, an internal diameter of 7.8 mm and a length of 300 mm (HPX 87H column—Biorad—Ref. 125.0140) was used. The conditions were the following: eluent 5 mN $H_2SO_4$ (1N sulfuric acid), flow rate of 0.8 ml/min.

The 3,4-DGE content was determined by liquid chromatography (using pyrazinecarboxamide (Sigma—Ref. P7136) for the calibration) and detection by UV spectrophotometry at 230 nm. For the chromatography, a column with a particle size of 5 μm, a pore size of 120 Å size, an internal diameter of 4.6 mm and a length of 15 cm (Supelcosil LC-18—Supelco—Ref. 58230) was used. The conditions were the following: elution solvent $H_2O$/MeOH, flow rate of 1.0 ml/min.

Figure 2:
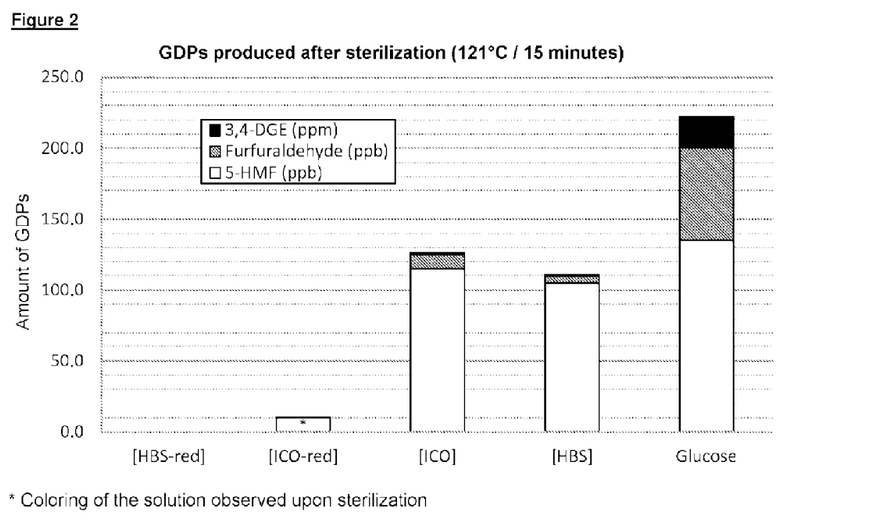
FIG. 2: Influence of sterilization on the production of GDPs, namely 5-hydroxymethylfuraldehyde (5-HMF), furaldehyde and 3,4-dideoxyglucosone-3-ene (3,4-DGE), of solutions using various glucose polymers or glucose (positive control).

The results are presented in FIG. 2.

As expected, the glucose produces a GDP content that is much higher than that of the glucose polymers. The [ICO] and [HBS] comparative glucose polymers exhibit contents which are lower but nevertheless high.

The [ICO-red] glucose polymer of U.S. Pat. No. 6,770,148, exhibits detectable contents of 5-HMF.

The glucose polymer in accordance with the invention [HBS-red] is the only one for which, after sterilization, the GDPs are not detectable.

These observations are all the more surprising since the pH for sterilization of the glucose polymer in accordance with the invention [HBS-red] is particularly high. This goes against the prior art teachings, which recommend sterilizing the solutions at acidic pH, precisely to avoid the formation of GDPs.

3. Effect of the Sterilization on the Reactivity with Respect to Proteins

In this example, the inventors studied the influence of sterilization on the reactivity with respect to proteins, of solutions using various glucose polymers or glucose.

Solutions containing 0.5% of each of the substances to be tested were prepared in a phosphate buffer (pH 7, 200 mM), in the absence or presence of 0.5% of L-lysine.

The absorbance of the solutions at 284 nm was measured before and after sterilization at 121° C. for 45 minutes.

The phosphate buffer used to prepare the solutions was used as a negative control.

Figure 3:
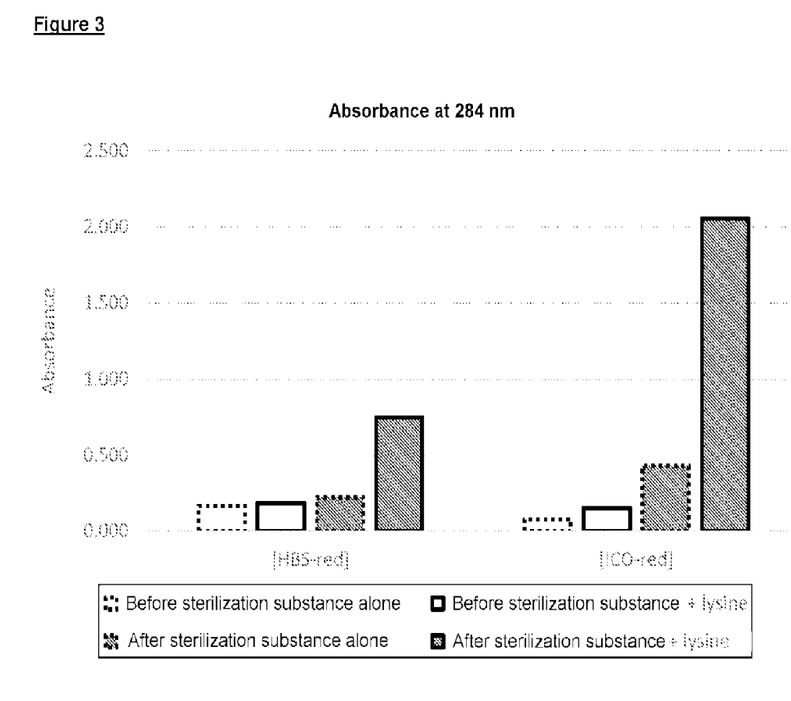
FIG. 3: Influence of sterilization on the reactivity with respect to proteins, of solutions using various glucose polymers or glucose (positive control) by measuring the absorbance at 284 nm.

The results obtained with the best two substances, that is to say [HBS-red] according to the invention and comparative [ICO-red] are presented in FIG. 3.

The difference in absorbance observed between the substance to be tested alone, before and after sterilization (dashed-line histograms) can be attributed to the production of degradation products. The results confirm the fact that the [HBS-red] glucose polymer of the invention is the substance which exhibits the greatest resistance to degradation during sterilization.

The difference in the absorbance observed between the substance to be tested in the presence and absence of lysine after sterilization (gray histograms) can be attributed to the reactions which occur between the substance to be tested and the lysine, thus reflecting the reactivity of these substances with respect to proteins (Maillard reaction). The higher the difference in absorbance, the more the substance can be judged to be reactive with respect to proteins. The results indicate that the [HBS-red] glucose polymer according to the invention is the substance that is the least reactive with respect to proteins. This very weaker reactivity points to an excellent tolerance of the glucose polymer of the invention.

The invention claimed is:

1. A glucose polymer characterized in that it is obtained by branching and reduction of a starch having an amylose content of at least 10%, and in that said glucose polymer has an α-1,6-bond content of less than 20%, a weight-average molecular weight (Mw) less than 50,000 Da, this Mw being determined by liquid chromatography and detection by differential refractometry, and a polydispersity index (polyD) of less than 3.0 and greater than 0.5; and wherein reduction results in the conversion of carbonyl groups to hydroxyl groups, and in that it has a reducing sugar content of less than 0.5%, this percentage being expressed by dry weight of reducing sugars relative to the total dry weight of the glucose polymer.

2. The glucose polymer as claimed in claim 1, characterized in that said glucose polymer has an α-1,6-bond content of greater than 7%.

3. The glucose polymer as claimed in claim 1, characterized in that said starch has an amylose content of at least 20%.

4. The glucose polymer as claimed in claim 1, characterized in that it has a weight-average molecular weight (Mw) chosen in the range of from 20,000 to 50,000 daltons (Da); this Mw being determined by liquid chromatography and detection by differential refractometry.

5. The glucose polymer as claimed in claim 1, characterized in that it has a pH, after sterilization at 121° C. for 45 minutes, in a range of from 6 to 8, when it is formulated as an aqueous 5% solution.

6. The glucose polymer as claimed in claim 1, characterized in that it has an osmolality of between 200 and 300 mOsm/kg; when it is formulated as a 0.4% solution.

7. The glucose polymer as claimed in claim 1, characterized in that it has a reducing sugar content of less than 0.1%, this percentage being expressed by dry weight of reducing sugars relative to the total dry weight of the glucose polymer.

8. The glucose polymer as claimed in claim 1, characterized in that it is soluble to very soluble in water when it is at ambient temperature.

9. The glucose polymer as claimed in claim 1, characterized in that it is not substituted.

10. A composition, comprising the polymer as defined claim 1.

11. The composition as claimed in claim 10, characterized in that it is a solution.

12. The glucose polymer as claimed in claim 1 or the composition as claimed in claim 11, for use thereof as a medicament.

13. The glucose polymer as claimed in claim 1 or the composition as claimed in claim 11, for use thereof in peritoneal dialysis, and/or parenteral nutrition, and/or in plasma filling, and/or as an osmotic agent, and/or as a plasma expander, and/or in vaccinology, and/or as an adjuvant, and/or as a protein stabilizer, and/or as a protein carrier.

14. A method for producing a composition as defined in claim 10, which comprises mixing a polymer as defined in claim 1 with at least one other substance and/or a solvent.

15. A method for producing a glucose polymer as defined in claim 1, which comprises subjecting a starch having an amylose content of at least 10% to:
   (a) a branching step; and
   (b) a reduction step.

* * * * *